United States Patent [19]

Roby et al.

[11] Patent Number: 5,902,874

[45] Date of Patent: May 11, 1999

[54] POLYESTERAMIDES FROM CYCLIC MONOMERS AND SURGICAL ARTICLES MADE THEREOF

[75] Inventors: Mark S. Roby, Killingworth; Ying Jiang, North Haven, both of Conn.

[73] Assignee: United States Surgical Corporation, Norwalk, Conn.

[21] Appl. No.: 08/999,643

[22] Filed: Jan. 28, 1998

Related U.S. Application Data

[XX .
[60] Provisional application No. 60/036,206, Jan. 28, 1997.

[51] Int. Cl.⁶ .................................................. C08G 69/44
[52] U.S. Cl. .......................... 528/310; 528/170; 528/322; 528/323; 528/327; 528/354; 528/355; 528/361; 525/411; 525/415; 525/417; 606/139; 606/228; 606/230

[58] Field of Search ..................................... 528/170, 310, 528/322, 323, 327, 354, 355, 361; 606/139, 228, 230; 525/417, 415, 411

[56] References Cited

U.S. PATENT DOCUMENTS

| | | | |
|---|---|---|---|
| Re. 30,170 | 12/1979 | Goodman et al. | 528/327 |
| 2,386,454 | 10/1945 | Frosch | 260/78 |
| 4,226,243 | 10/1980 | Shalaby | 128/335.5 |
| 4,343,931 | 8/1982 | Barrows | 528/291 |
| 5,349,045 | 9/1994 | Jiang | 528/323 |
| 5,446,108 | 8/1995 | Jiang | 528/417 |
| 5,480,961 | 1/1996 | Jiang et al. | 528/220 |
| 5,483,009 | 1/1996 | Jiang | 525/417 |

*Primary Examiner*—P. Hampton-Hightower

[57] ABSTRACT

Cyclic monomers prepared by novel methods are useful in making polyesteramides which can be made into shaped articles, particularly, shaped articles suitable for use as surgical devices.

30 Claims, No Drawings

POLYESTERAMIDES FROM CYCLIC MONOMERS AND SURGICAL ARTICLES MADE THEREOF

This application claims benefit of Provisional Application Ser. No. 60/036,206 filed Jan. 28, 1997.

TECHNICAL FIELD

Polyesteramides prepared from cyclic monomers and methods for their preparation are described herein. The polyesteramides are suitable for use in forming shaped articles, such as, for example, surgical devices.

BACKGROUND

Polyesteramides are polymers containing both ester linkages and amide linkages. Their significance for technology of surgical devices stems from the fact that the susceptibility of their ester linkages to hydrolysis confers upon them the ability to be eventually absorbed, or resorbed by a body into which they have been implanted and their amide linkages confer upon them the desirable mechanical properties characteristic of polyamides.

Fiber-forming polyesteramides obtained from the single stage reaction of approximately equimolar amounts of a monoalkanolamine and a dicarboxylic acid are known from U.S. Pat. No. 2,386,454. Polyesteramides indicated to be useful for the manufacture of absorbable sutures and other surgical devices are disclosed in U.S. Pat. No. 4,226,243 as obtained from the reaction of a bis-oxyamidodiol (itself derived from the reaction of diethyl oxalate with a monoalkanolamine such as ethanolamine) with a dicarboxylic acid ester. U.S. Pat. No 4,343,931 discloses absorbable surgical devices manufactured from polyesteramides obtained by reacting a diamine with lactic or glycolic acid to produce a diamidediol, which is then reacted with a bischloroformate or a compound selected from the group consisting of dicarboxylic acids, diacidchlorides and dicarboxylic acid anhydrides.

Nylon refers to a family of high strength, resilient synthetic materials, the long chain molecules of which contain recurring amide groups. Nylon has been widely accepted for a variety of applications. Certain surgical applications, however, require a surgical device that is bioabsorbable. Nylon is not bioabsorbable and is therefore unacceptable in such circumstances.

It would be desirable to provide a surgical device that has strength and resiliency characteristics similar to those of nylon, but which is bioabsorbable.

SUMMARY

It has now been found that polyesteramides derived from cyclic monomers are useful in making shaped articles, particularly, shaped articles suitable for use as surgical devices. The cyclic monomers are of the formula:

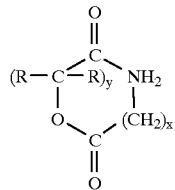

where x is an integer from 1 to 3 and y is an integer from 1 to 3 and R can be the same or different at each occurrence and is individually selected from the group consisting of hydrogen and $C_1$ to $C_4$ alkyl. Preferably, R is hydrogen at each occurrence and x+y=3.

Two novel methods are described herein for making the cyclic monomers. The first method of making the present cyclic monomers involves blocking the amino group of the amino acid, reacting with a hydroxy acid, removing the blocking group and then performing a ring closure reaction. The cyclic monomer can then be purified and polymerized to form the polyesteramide.

The second method for preparing the cyclic monomers involves reacting an amino acid with a hydroxy alklanoyl halide halogenating the resulting product and then performing a ring closure reaction. The cyclic monomer can then be purified and polymerized to form the polyesteramide.

The resulting polyesteramide can be bioabsorbable and can be formed into shaped articles, for example by molding or extrusion. Particularly useful shaped articles include surgical devices such as sutures and other surgical implants.

DETAILED DESCRIPTION OF PREFERRED EMBODIMENTS

The cyclic monomers for making polyesteramides have the following general formula:

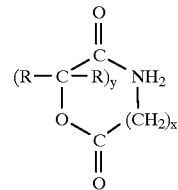

wherein x is an integer from 1 to 3 and y is an integer from 1 to 3 and R can be the same or different at each occurrence and is individually selected from the group consisting of hydrogen and $C_1$ to $C_4$ alkyl. The polyesteramides produced from the cyclic monomers described herein have the following general formula:

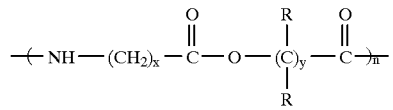

where x, y and R are as defined above.

In particularly useful embodiments, R is hydrogen at each occurrence. In such embodiments, the resulting polyesteramide has the general formula:

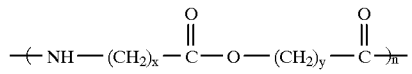

The cyclic monomer can be prepared in any manner known to those skilled in the art. In a particularly useful embodiment, the cyclic monomers are prepared using a novel reaction scheme that involves blocking the amino group of the amino acid, reacting with a hydroxy acid, removing the blocking group and then performing a ring closure reaction. The cyclic monomer can then be purified and polymerized to form the polyesteramide.

In this reaction scheme, suitable starting materials include amino acids of the formula:

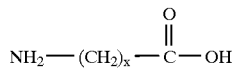

where x is an integer from 1 to 3. The amino acids wherein x is 1 or 2 is a particularly useful starting material.

The first step in making the cyclic monomer is to block the amino group of the amino acid. This will ensure that subsequent reaction with a hydroxy acid occurs only at the acid group of the amino acid. Introduction of a blocking agent onto the amino group can be accomplished using any of the techniques known to those skilled in the art. Suitable blocking agents include benzyl chloroformate. Benzyl chloroformate can be reacted with the amino acid in the presence of a metal oxide (e.g., MgO) in an aqueous ether solution at reduced temperatures (e.g., around 5 degrees C.).

The protected amino acid is then converted to an acid halide. This can be achieved, for example, by refluxing the protected amino acid with $SOX_2$ wherein X is F, Br, Cl or I, in methylene chloride.

The acid halide is reacted with a hydroxy acid. Suitable hydroxy acids include those of the formula:

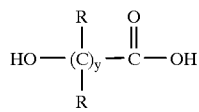

wherein y is an integer from 1 to 3 and R can be the same or different at each occurrence and is individually selected from the group consisting of hydrogen and $C_1$ to $C_4$ alkyl. Alpha-hydroxy acids in general, and glycolic acid in particular are the preferred hydroxy acids for making the cyclic monomers described herein. The reaction of the acid halide with the hydroxy acid can be carried out by refluxing in the presence of an inert diluent such as, for example, DMF and a tertiary amine, such as, for example, triethylamine (TEA).

The blocking agent is then removed using techniques known to those skilled in the art. For example, if benzyl chloroformate is used as the blocking agent, the blocking agent can be removed by reacting with HBr in acetic acid.

The resulting product has the general formula:

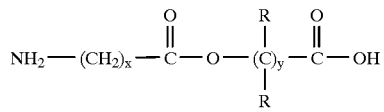

where x, y and R are as defined above. Preferably, x+y=3.

This reaction product is then subjected to a ring closure reaction. For example, the product is heated in the presence of a metal catalyst such as, for example, stannous octoate. The cyclic monomer is then isolated and purified.

A second reaction scheme useful in preparing the cyclic monomers described herein involves reacting an amino acid with a hydroxy alkanoyl chloride to produce an amino acid with an ester linkage, halogenating that compound and then performing a ring closure reaction. The cyclic monomer can then be purified and polymerized to form the polyesteramide.

In this second reaction scheme, suitable starting materials include amino acids of the formula:

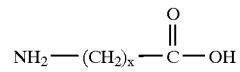

where x is an integer from 1 to 3.

The amino acid is reacted with a hydroxy alkanoyl halide of the general formula:

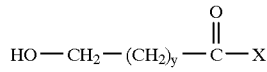

where X is F, Cl, Br or I and y is an integer from 0 to 3. This reaction can be achieved, for example by refluxing in the presence of an inert diluent such as, for example, DMF and a tertiary amine, such as, for example, triethylamine (TEA). The resulting product is a amino acid with an ester linkage of the formula:

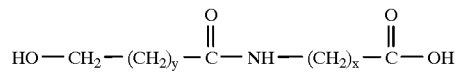

where x and y are as defined above.

This compound is then halogenated, for example by reacting with $SOX_2$ where X is F, Cl, Br or I, in methylene chloride to provide a compound of the formula:

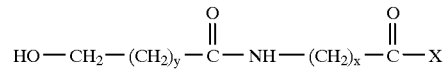

where x and y are as defined above.

This halogenated compound can then be subjected to a ring closure reaction. For example, the above halogenated compound can be reacted in an THF and TEA at reduced temperatures (e.g., around 5 degrees C) to produce ring closure. The cyclic monomer is then isolated and purified.

The cyclic monomer should be purified, preferably to at least about 98 percent purity prior to polymerization. The monomer may be purified using any known technique such as multiple distillations and/or recrystallizations.

The cyclic monomer can be polymerized by heating in the presence of initiators such as alcohols or aminoalkanols and a metal catalyst (e.g., $Sn(Oct)_2$) to produce a ring-opening polymerization reaction.

If desired, any portion of the cyclic monomer employed in the polymerization reaction, e.g., from about 1 to about 99 mole percent can be replaced with a like mole percentage of another difunctional reactant such as hydroxycarboxylic acid or lactone precursor thereof, e.g., glycolide, lactide, gamma-butyrolactone, epsilon-caprolactone, etc.

The polyesteramides can be formed into surgical articles using any know technique, such as, for example, extrusion, molding and/or solvent casting. The polyesteramides can be used alone, blended with other absorbable compositions, or in combination with nonabsorbable components. A wide variety of surgical articles can be manufactured from the polyesteramides described herein. These include but are not limited to clips and other fasteners, staples, sutures, pins, screws, prosthetic devices, wound dressings, drug delivery devices, anastomosis rings, and other implantable devices. Fibers made from the present polyesteramides can be knitted or woven with other fibers, either absorbable or nonabsorbable to form meshes or fabrics. Compositions including these polyesteramides can also be used as an absorbable coating for surgical devices.

Optional additives which may be present in compositions made from the polyesteramides described herein include plasticizers, release agents and other processing aids. Where the composition is used to make a surgical device, stearic acid or calcium stearate are particularly useful additives due to their biocompatibility.

In another aspect, compositions containing the polyesteramides described herein can be used to make reinforced composites. Thus, for example, the polyesteramide composition can form the matrix of the composite and can be reinforced with bioabsorbable or nonabsorbable fibers or particles. Alternatively, a matrix of any bioabsorbable or non-bioabsorbable polymer composition can be reinforced with fibers or particulate material made from compositions containing the polyesteramides described herein.

In an alternative embodiment, the polyesteramides described herein are admixed with a filler. The filler can be in any particulate form, including granulate and staple fibers. While any known filler may be used, hydroxyapatite, tricalcium phosphate, bioglass or other bioceramics are the preferred fillers. Normally, from about 10 grams to about 400 grams of filler are mixed with 100 grams of polymer. The filled, cross-linked polymers are useful, for example, as a molding composition.

It is further contemplated that one or more medico-surgically useful substances can be incorporated into compositions containing the polyesteramides described herein. Examples of such medico-surgically useful substances include, for example, those which accelerate or beneficially modify the healing process when particles are applied to a surgical repair site. So, for example, articles made from the composition can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is also contemplated that it may be desirable to dye articles made from compositions containing the polyesteramides in order to increase visibility of article in the surgical field. Dyes, such as those known to be suitable for incorporation in sutures, can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, articles made in accordance with this disclosure are dyed by adding up to about a few percent and preferably about 0.2% dye, such as D&C Violet No. 2 to the resin prior to extrusion.

It will be understood that various modifications may be made to the embodiments disclosed herein. Therefore the above description should not be construed as limiting, but merely as exemplifications of preferred embodiments. Those skilled in the art will envision other modifications within the scope and spirit of the claims appended hereto.

What is claimed is:

1. A compound of the general formula:

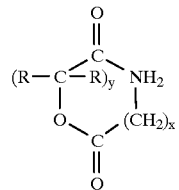

wherein x is an integer from 1 to 3 and y is an integer from 1 to 3 and R can be the same or different at each occurrence and is individually selected from the group consisting of hydrogen and $C_1$ to $C_4$ alkyl.

2. A compound in accordance with claim 1 wherein R at each occurrence is hydrogen.

3. A compound in accordance with claim 1 wherein x+y=3 and R at each occurrence is hydrogen.

4. A compound in accordance with claim 1 wherein x=2, y=1 and R at each occurrence is hydrogen.

5. An esteramide compound comprising repeating units derived by ring-opening polymerization of a compound in accordance with claim 1.

6. An esteramide compound in accordance with claim 5 consisting essentially of repeating units of the general formula:

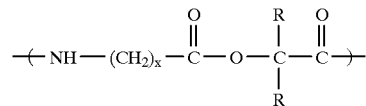

wherein x is an integer from 1 to 3 and R can be the same or different at each occurrence and is individually selected from the group consisting of hydrogen and $C_1$ to $C_4$ alkyl.

7. An esteramide compound in accordance with claim 5 further comprising repeating units derived from one or more monomers selected from the group consisting of hydroxycarboxylic acids and lactone precursors thereof.

8. An esteramide compound in accordance with claim 5 wherein R at each occurrence is hydrogen.

9. An esteramide compound in accordance with claim 5 wherein x+y=3 and R at each occurrence is hydrogen.

10. An esteramide compound in accordance with claim 5 wherein x=1, y=2 and R at each occurrence is hydrogen.

11. A method of making a cyclic monomer for producing a polyesteramide comprising:
    a) blocking the amino group of an amino acid;
    b) halogenating the blocked amino acid to provide a halogenated acid;
    c) reacting the halogenated acid with a hydroxy acid to provide a monomer;
    d) de-blocking the product from step c); and
    e) subjecting the product of step d) to a ring closure reaction.

12. A method in accordance with claim 11 wherein step a) comprises blocking the amino group of an amino acid of the general formula:

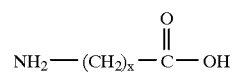

where x is an integer from 1 to 3.

13. A method in accordance with claim 11 wherein step a) comprises reacting an amino acid with benzyl chloroformate.

14. A method in accordance with claim 11 wherein step b) comprises reacting the blocked amino acid with a compound of the formula $SOX_2$ wherein X is selected from the group consisting of F, Cl, Br and I.

15. A method in accordance with claim 11 wherein step b) comprises chlorinating the blocked amino acid.

16. A method in accordance with claim 11 wherein step d) comprises reacting the acid halide with an alpha-hydroxy acid of the general formula:

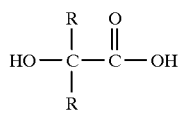

wherein R can be the same or different at each occurrence and is individually selected from the group consisting of hydrogen and $C_1$ to $C_4$ alkyl.

17. A method in accordance with claim 11 wherein step d) comprises reacting the acid halide with glycolic acid.

18. A method of making a polyesteramide comprising:
    preparing a cyclic monomer in accordance with claim 11;
    polymerizing the cyclic monomer to produce a polyesteramide.

19. A method in accordance with claim 18 wherein the polyesteramide produced consists essentially of repeating units of the general formula:

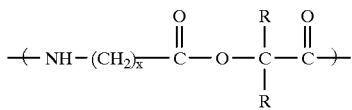

wherein x is an integer from 1 to 3 and R can be the same or different at each occurrence and is individually selected from the group consisting of hydrogen and $C_1$ to $C_4$ alkyl.

20. A composition comprising:
    an esteramide compound in accordance with claim 5.

21. A composition in accordance with claim 20 wherein the esteramide has at least one unit of the general formula:

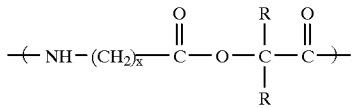

wherein x is an integer from 1 to 3 and R can be the same or different at each occurrence and is individually selected from the group consisting of hydrogen and $C_1$ to $C_4$ alkyl.

22. A composition in accordance with claim 20 further comprising at least one medico-surgically useful compound.

23. A composition in accordance with claim 20 further comprising a plasticizer.

24. A composition in accordance with claim 20 further comprising a filler.

25. A composition in accordance with claim 20 further comprising one or more bioabsorbable polymer selected from the group consisting of homopolymers and copolymers of glycolide, lactide, trimethylene carbonate, dioxanone and caprolactone blended with the esteramide compound.

26. A composition in accordance with claim 20 wherein the esteramide compound consists essentially of repeating units of the general formula:

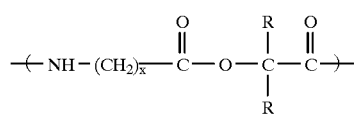

wherein x is an integer from 1 to 3 and R can be the same or different at each occurrence and is individually selected from the group consisting of hydrogen and $C_1$ to $C_4$ alkyl.

27. A composition in accordance with claim 20 wherein the esteramide compound consists essentially of repeating units of the general formula:

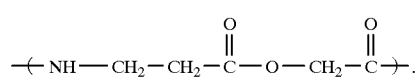

28. A composition in accordance with claim 20 wherein the esteramide compound consists essentially of repeating units of the general formula:

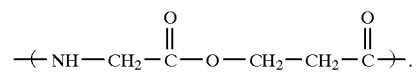

29. A surgical device comprising a shaped article made from the compound of claim 5.

30. A surgical device comprising a shaped article made from the composition of claim 20.

* * * * *